US006221402B1

(12) United States Patent
Itoh et al.

(10) Patent No.: US 6,221,402 B1
(45) Date of Patent: Apr. 24, 2001

(54) RAPIDLY RELEASING AND TASTE-MASKING PHARMACEUTICAL DOSAGE FORM

(75) Inventors: Akinori Itoh, Taketoyo-cho; Toshiyuki Niwa, Handa, both of (JP)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/341,312

(22) PCT Filed: Nov. 20, 1997

(86) PCT No.: PCT/IB97/01471

§ 371 Date: Sep. 20, 1999

§ 102(e) Date: Sep. 20, 1999

(87) PCT Pub. No.: WO98/30209

PCT Pub. Date: Jul. 16, 1998

(51) Int. Cl.$^7$ ........................................................ A61K 9/14
(52) U.S. Cl. .......................... 424/494; 424/490; 424/493; 424/495; 424/497; 514/781; 514/951
(58) Field of Search ..................................... 424/489, 464, 424/465, 451, 452, 455, 458, 459, 461, 462, 493, 494, 497, 490, 495

(56) References Cited

FOREIGN PATENT DOCUMENTS

| | | | |
|---|---|---|---|
| 0409254 | 1/1991 | (EP) | ................................. A61K/9/14 |
| 0458751 | 11/1991 | (EP) | ............................. A61K/31/195 |
| 63-258809 | 10/1988 | (JP) | ............................... A61K/9/50 |
| 6-56700 | 3/1994 | (JP) | .............................. A61K/47/38 |
| 2576927 | 1/1997 | (JP) | .............................. A61K/47/38 |
| 9601623 | 6/1995 | (WO) | ............................... A61K/9/26 |

OTHER PUBLICATIONS

Merck Index, 11th Merck & Co. NJ, 1989, pp. 935.
Remington farmacia Practica, Second Spanish Ed. pp. 510, 511, 512 Editorial Utheha 1985.
Database WPI; Section Ch, week 9413, Derwent Publications, Ltd., London, GB; Class A96, AN 94–106744; XP002059781.
Database WPI; Section Ch, Week 8849, Derwent Publications Ltd., London, GB; Class A96, AN 88–348774, XP002059782.

*Primary Examiner*—James M. Spear
(74) *Attorney, Agent, or Firm*—Peter C. Richardson; Gregg C. Benson; Michelle A. Sherwood

(57) ABSTRACT

A rapidly-releasing and taste-masking pharmaceutical dosage form and a process for preparing such oral dosage form are disclosed.

9 Claims, No Drawings

RAPIDLY RELEASING AND TASTE-MASKING PHARMACEUTICAL DOSAGE FORM

This is a National Stage filing under 35 USC §371 based on PCT/IB97/01471 which was filed internationally on Nov. 20, 1997.

TECHNICAL FIELD

This invention relates to rapidly releasing and taste-masking pharmaceutical dosage form, and a process for preparation thereof. More specifically, this invention relates to a pharmaceutical dosage form which can be orally administered without bitter taste, with improved drug release properties in a gastrointestinal tract.

BACKGROUND ART

The bitter taste of many drugs which are orally administered are disadvantageous in several aspects. For example, the disagreeable taste of drugs causes difficulties in swallowing or causes patients to avoid taking their medication, whereby resulting in low compliance of patients. Thus, taste-masking technologies are considered very important, and are being developed by many researchers. The taste-masking is usually achieved by forming a taste-masking layer on a particle having an active ingredient. However, the taste-masking layer may cause poor drug release profiles. Thus, the formulation design is difficult to provide oral dosage forms having good taste-masking properties and good drug release properties.

European Patent Application No. EP 0409254 discloses rapid-releasing oral particle pharmaceutical preparation with unpleasant taste masked. The oral particle pharmaceutical preparation comprises a core and a film layer coating the core, the core at least containing a drug having an unpleasant taste and a water-swelling agent, and the film layer at least containing ethylcellulose and a water-soluble substance. However, this technology usually requires the heating of final product (e.g., at 60–75° C., 10–20 hr) to attain good drug release properties. The heating treatment is not preferable for heat-sensitive drugs which may be decomposed or melt at such high temperature. Further, in this technology, the effective masking time is described as more than 20 seconds. Such time period is not enough to provide complete masking effect for some patinets such as those with artificial teeth. Also, the previous technology cannot avoid the use of acetone and chlorine solvent (e.g., methyene chloride), which is harmful to human bodies, to provide the sufficient masking effect.

Japanese Patent Application Laid-Open Publication No. S63-258809 discloses fine granules prepared by forming 1 to 10 wt. % of an outer layer on a core particle having a bitter active ingredient, and forming 3 to 10 wt. % of a saliva-insoluble layer on the outer layer. However, this technology cannot provide fine granules having rapid release properties in neutral and alkalic pH media. This is because the polymer composed of the outer layer has solubility strongly dependent on pH in media, and cannot be dissolved and disrupted in the neutral and alkalic pH media.

Accordingly, it would be desired if oral dosage form having improved drug release properties and taste-masking properties were provided.

BRIEF DISCLOSURE OF THE INVENTION

The present invention provides a rapidly releasing and taste-masking pharmaceutical dosage form (or pharmaceutical preparation) comprising a core containing a pharmaceutically active ingredient, low-substituted hydroxypropyl cellulose and microcrystalline cellulose, the amount of the microcrystalline cellulose being at least 26.0 weight percent based on the total weight of the core; an inner coating layer formed on the core and containing a water-soluble polymer; and an outer coating layer formed on the inner coating layer and containing a saliva-insoluble polymer. In the dosage form of this invention, the core, the inner coating layer and the outer coating layer are preferably contained in an amount of from 49.9 to 95.1, from 0.1 to 45.3 and from 4.8 to 50.0 weight percent, respectively, based on the total weight of the dosage form. The dosage form may further comprises a sugar coating layer formed on the outer coating layer. The core is preferably in a spherical form and has an average particle diameter of 80 to 400 micrometers, more preferably 100 to 300 micrometers.

Suitable inner coating layer comprises 70.0 to 100 weight percent of a water-soluble polymer such as hydroxypropylmethyl cellulose, and up to 30.0 weight percent of a water-insoluble polymer such as (1) an ethyl acrylate/methyl methacrylate copolymer, (2) an ethyl acrylate/methyl methacrylate/trimethylammonioethyl methacrylate copolymer. Suitable outer coating layer comprises 70.0 to 100 weight percent of a saliva-insoluble polymer such as (3) a buthyl methacrylate/(2-dimethylaminoethyl) methacrylatelmethyl methacrylate copolymer, and up to 30.0 weight percent of a water-soluble or water-insoluble copolymer.

According to the present invention, oral dosage forms having improved drug release properties and taste-masking properties (for example, more than 50 seconds) can be provided.

The present invention also provides a process for preparing the dosage form as mentioned above, which comprises mixing core materials containing a pharmaceutically active ingredient, low-substituted hydroxypropyl cellulose and microcrystalline cellulose and subject the mixed core materials to wet agitation granulation, dry treatment and sieving treatment in this order to obtain core particles; forming an inner coating layer on the core particles by spraying with an aqueous solution containing a water-soluble polymer; and then forming an outer coating layer on the inner coating layer by spraying with an aqueous solution containing a saliva-insoluble polymer. This process can be carried out in the absence of a solvent harmful to a human body (e.g., acetone and chlorine solvent such as methylene chloride, chloroform and methyl chloride). Thus, this process is advantageous in view of safety and ecology.

DETAILED DESCRIPTION OF THE INVENTION

In the present invention, the oral dosage form comprises at least three layers, i.e., a core (also referred to as core particle) containing a pharmaceutically active ingredient, low-substituted hydroxypropyl cellulose and microcrystalline cellulose; an inner coating layer containing a water-soluble polymer; and an outer coating layer containing a saliva-insoluble polymer.

Active ingredients which usually used in this invention have a bitter taste, although those having no bitter taste can also be used. Active ingredients useful in this invention include, for example, antifungal agents such as fluconazole, pain relievers such as acetaminophen and acetylsalicylic acid, antihistamines such as diphenhydramine, doxylamine succinate and meclizine, decongestants such as pseudoephedrine hydrochloride, anti-impotence such as sildenafil, antibiotics such as azithromycin, erythromycin and cepholosporin, penicillins such as sultamicillin tosylate and amoxicillin trihydrate, enzyme inhibitors such as sulbactam sodium, anthihypertensives such as nifedipine, doxazosin mesylate and arnlodipine besylate, antidiabetics such as glipizide, bronchodilators such as pirbuterol hydrochloride and theophyfline, anti-inflammatory agents such as piroxicam and tenidap, anti-depressants such as sertaraline hydrochloride, antacids such as calcium carbonate and magnesium oxide, and non-sedative antihistamines such as cetirizine, cardiotonics such as digitoxin and digoxin.

As used herein, "microcrystalline cellulose" means purified, partially depolymerized cellulose prepared by treating alpha cellulose. Examples of the microcrystalline cellulose are those soled under the tradename of Avicel™ (manufactured by Asahi Chemical Industry), Ceolus™ (manufactured by Asahi Chemical Industry), Vivacel™ (manufactured by J. Rettenmaier & Sohne GmbH), and Emcocel™(manufactured by Edward Mendell Co. Inc.). Suitable microcrystalline celluloses include those sold under the trade name of Avicel™ PH-101, PH- 102, PH-301 and PH-302 (manufactured by Asahi Chemical Industry), and mixtures of two or more of these celluloses. Most preferred are Avice™ PH-101.

As used herein, "low-substituted hydroxypropyl cellulose" means a low-substituted poly (hydroxypropyl) ether of cellulose, which contains not less than 5.0% and not more than 16.0 % of hydroxypropoxy groups on a dried basis. Examples of low-substituted hydroxypropyl cellulose include one sold under the trade name of LH-31 (manufactured by Shin-Etsu Co. Ltd.)

If desired, the other additives may be added to the above-mentioned core materials. Such additives include a binder such as hydroxypropyl methyl cellulose, or hydroxypropyl cellulose, a masking agent such as calcium gluconate, magnesium oxide and a lubricant such as talc and magnesium stearate.

The core particles used in this invention are preferably in a spherical form, and has an average particle diameter of 80 to 400 micrometers, more preferably 100 to 300 micrometers. Preferably, the cores may have a sphericity of 0.85 to 1.0, more preferably 0.9 to 1.0. The spherical core particles used in this invention are advantageous in that coating efficiency can be improved in subsequent coatings of an inner layer and an outer layer.

Suitable cores (also referred to as core particles) used in the present invention comprises 0.1 to 73.5, more preferably 20.0 to 40.0 of the active ingredient; 26.0 to 99.4, more preferably 28.0 to 80.0, most preferably 30.0 to 60.0 weight percent of the microcrystalline cellulose; and 0.5 to 34.0, more preferably 3.0 to 30.0 weight percent of the low-substituted hydroxypropyl cellulose, the weight percent being based on the total weight of the core material. Use of core particles with these component ratios may give good drug release profiles. When the amount of the microcrystalline cellulose is outside of the above-mentioned level, the sphericity of the resultant core particles may be decreased, resulting in decrease in coating efficiency.

In the present invention, an inner coating layer is formed on the above-mentioned core particles. The purpose of formation of the inner coating layer is smoothing of core surface and easy separation of the outer coating layer from an acidic solution of an active ingredient such as sildenafil citrate (about pH3.85). Suitable inner coating layer comprises 70.0 to 100 weight percent of a water-soluble polymer, and up to 30.0 weight percent of a water-insoluble polymer.

As used herein, the term "water-soluble polymer" means a conventional polymer for pharmaceutical use, having a solubility of more than 10 mg/ml in water. Suitable water-soluble polymers include, for example, hydroxypropylmethyl cellulose, hydroxypropyl cellulose, polyvinyl pyrolidore and polyvinyl alcohol. Most preferred water-soluble polymers used in this invention are hydroxypropylmethyl cellulose and hydroxypropyl cellulose. As used herein, the term "water-insoluble polymer" means a conventional polymer for pharmaceutical use, having a solubility of not more than 10 mg/ml in water. Suitable water-insoluble polymers include, for example, ethylcellulose, methacrylate copolymers and aminoalkyl methacrylate copolymers such as an ethyl acrylate/methyl methacrylate copolymer and an ethyl acrylate/methyl methacrylate/trimethylammonioethyl methacrylate copolymer. Commercially available water-insoluble polymers may be used. Such water-insoluble polymers are those sold under the trade name of Aquacoat (manufactured by Asahi Chemical Industry) Eudragit NE and Eudragit RS (manufactured by Röhm Pharma).

If desired, the other additives may be added to the inner coating materials. Such additives include, for example, a lubricant such as magnesium stearate or talc.

Then, an outer coating layer is formed on the above-mentioned inner layer. The outer coating layer mainly has a taste-masking effect to prevent an active ingredient from being released when a patient hold a coated drug in his mouth. Suitable outer coating layer comprises 70.0 to 100 weight percent of a saliva-insoluble polymer and up to 30.0 weight percent of a water-soluble or water-insoluble polymer, the weight percent being based on the total weight of the outer coating layer. As used herein, the term "saliva-soluble polymer" means a conventional synthetic polymer for pharmaceutical use, having a solubility of less than 10 mg/ml in neutral pH (6.0–7.5) and more than 10 mg/ml in acidic pH (1.2–5.0). Suitable saliva-insoluble polymers include, for example, aminoalkyl methacrylate copolymers such as a buthyl methacrylate/(2-dimethylaminoethyl) methacrylate/methyl methacrylate copolymer and polyvinylacetal diethylaminoacetate. Commercially available polymers may be used. Such polymers are those sold under the trade name of Eudragit E (manufactured by Röhm Pharma) and the trade name of AEA (Sankyo) (manufactured by Sankyo). Suitable water-soluble polymers used as outer coating materials include, for example, hydroxypropylmethyl cellulose and hydroxypropyl cellulose. Suitable water-insoluble polymers used as inner coating materials include, for example, ethylcellulose and Eudragit RS.

In the oral dosage forms of the present invention, the core, the inner coating layer and the outer coating layer may be contained in an amount of from 49.9 to 95.1 (more preferably from 60.0 to 87.0), from 0.1 to 45.3 (more preferably from 4.0 to 31.0, most preferably from 4.0 to 10.0) and from 4.8 to 50.0 (more preferably from 9.0 to 36.0) weight percent, respectively, based on the total weight of the dosage form. The component ratio may be determined depending on the kind of active ingredient used, the kind of polymers used, desired drug release profile and the like. In general, the resultant coated drugs with the above component ratio, may give good drug release profiles and taste-masking effects.

The process for preparing the above-mentioned oral dosage forms will be described below.

Firstly, a core or core particles may be prepared by mixing core materials containing a pharmaceutically active ingredient, low-substituted hydroxypropyl cellulose and microcrystalline cellulose and subject the mixed core materials to wet agitation granulation, dry treatment and sieving treatment in this order. Methods for preparing the core particles, which can be used in this invention, are well described in Kokai H06-56700. For example, powders of an active ingredient such as sildenafil citrate is mixed with microcrystalline cellulose, L-HPC and other additives such as a masking agent (e.g., calcium gluconate), binder (e.g. hydroxypropyl methyl cellulose), lubricant (e.g., talc), in a vessel of the granulator. Then, the mixture is granulated for 10 to 60 minutes after addition of water at room temperature by a wet agitation granulation method known to those skilled in the art. The granulated core particles may be dried with a fluidized bed dryer and sieved, to obtain substantially spherical core particles. Preferably, the core particles may be fractionated to obtain fine particles having an average particle size of 80 to 400, preferably 100 to 300 micrometers.

Then, the core particles thus prepared may be coated with an inner coating layer on the core particles by spraying with an aqueous solution containing a water-soluble polymer; and then coated with an outer coating layer on the inner coating layer by spraying with an aqueous solution containing a saliva-insoluble polymer.

The core particles may be coated by spraying with an aqueous solution composed of a water-soluble polymer, water-insoluble polymer, water and other additives such as talc in a centrifugal fluidizing granulator (e.g., CF-Granulator under the trade name of CF-360 manufactured by Freund, Inc.). The coating conditions may be determined depending on the kind of granulator used, the kind of ingredients, component ratio and the like. Suitable conditions, when using the above CF-Granulator, may be a slit air temperature of 30 to 70° C.; a slit air rate of 200 to 350 l/min; a rotating speed of 100 to 200 rpm; a spray speed of 2 to 7 g/min; and a spray air pressure of 2 to 4 kg/Cm$^2$. After spray, the particles may be dried with, for example, a fluidized bed dryer or tray dryer.

Further, the core particles may be coated by spraying with an aqueous ethanolic solution (e.g., 80% EtOH) composed of a saliva-insoluble polymer, ethanol, water and other additives such as talc in a centrifugal fluidizing granulator (e.g., CF-Granulator under the tradename of CF-360 manufactured by Freund, Inc.). The coating conditions may be determined depending on the kind of granulator used, the kind of ingredients, component ratio and the like. The similar conditions as mentioned above may be used. After spray, the particles may be dried with, for example, a fluidized bed dryer, and then oven-cured, to obtain three-layer core particles of this invention.

In addition, to achieve a good taste and mouth feeling, a sugar coating layer may be formed on the outer coating layer of the three layer particles thus prepared. A known coating method can be used to form such sugar coating layer. For example, the three layer particles may be fed by spray solution composed of sucrose and D-mannitol dissolved in water under reasonable conditions. Xanthan gum (a polysaccharide generated from natural source) may be added to provide a good mouth feeling. The amount of the sugar coating layer may be in a range of 15.0 to 270.0 weight percent based on the total weight of the coated particle composed of the core, the inner and outer coating layers. The pharmacological dosage forms of this invention can be used in the form of fine granules, tablets, POS (powder for oral suspension), capsules or the like.

EXAMPLES AND COMPARATIVE EXAMPLES

The present invention will be described in more details with reference to the following Working and Comparative Examples.
(Materials Used)
The following materials were used in the Working and Comparative Examples.
Core Material
   Active Ingredient: Sildenafil citrate
   L-HPC: Low-substituted hydroxypropyl cellulose (LH-31; Shin-Etsu)
   MCC: Microcrystalline cellulose (Avicel PH101, Asahi Chemical Industry)
   HPMC: Hydroxypropyl methyl cellulose2910 as a binder (TC-5E, Shin-Etsu)
   Calcium gluconate (Tomita Pharmaceuticals).
Inner Coating Layer
   Water-Soluble polymer:
   MPMC: Hydroxypropyl methyl cellulose2910 (TC-5E, Shin-Etsu)
   Water-insoluble polymer: methacrylate copolymer (Eudragit NE30D, Röhm Pharma)
Outer Coating Layer
   Saliva-insoluble polymer: aminoalkyl methacrylate copolymer under the trade name of Eudragit E100, (Röhm Pharma).
   When needed, other excipients such as talc and magnesium stearate, hydroxypropyl methyl cellulose and ethylcellulose, are added.

Example 1
(1) Manufacturing of Core Particles
   An active ingredient (sildenafil citrate, 210.66 g) was mixed with microcrystalline cellulose(300 g), L-HPC(97.2 g), calcium gluconate(64.8 g), and hydroxypropyl methyl cellulose2910(7.2 g) as a binder in a vessel of the granulator. The amount ratio of the components used are indicated in Table 1. Then, the mixture was granulated by a wet agitation granulation method (Vertical Granulator, VG-05, Powrex) for 30 min after addition of water (699.0 g) at room temperature (blade speed, 200 rpm; cross screw speed, 3600 rpm). The granulated cores were dried with a fluidized bed dryer (FBD) (Multiplex, MP-01, Powrex, Japan) and sieved to obtain core particles having an average diameter of 177–297 micrometers.
   The fractionated core fine particles (177–297 mm) were coated with three layers (inner layer, outer layer, sugar layer) by using a centrifugal fluidizing granulator (CF-Granulator, CF-360, Freund).
(2) Coating of Inner Layer
   The core particles (360.0 g) prepared in the above Step (1) were coated by spraying with the coating solution composed of TC-5E(30.2 g), Eudragit NE30D(20.1 g) and 378.2 g of water in a centrifugal fluidizing granulator (CF-Granulator, CF-360, Freund). Talc and magnesium stearate were added to protect the electrostatic aggregation of each particles. The amount ratio of the components used are indicated in Table 1. The conditions used were as follows: slit air temperature, 70° C.; slit air rate, 250 l/min; rotating speed, 150 rpm, spray speed, 3.4 g/min; and spray air pressure, 3.0 kg/cm$^2$. After spray, the particles were dried with fluidized bed dryer (Multiplex, MP-01, Powrex) for 25 min (inlet, 80° C. outlet, 50° C.).

(3) Coating of Outer Layer

Eudragit E100(66.5 g), which was dissolved in 950.2 g of aqueous ethanolic solution (80% EtOH), was applied to coat on the inner layer-coated particles (190.0 g) with a CF-Granulator (slit air temperature, 34° C.; slit air rate, 300 l/min; rotating speed, 140 rpm; spray speed, 5.0 g/min). The coating level of the outer layer was adjusted as indicated in Table 1. After spray, the particles were transferred to FBD and oven-cured at the same conditions described above to increase the protect effect to obtain three layer products.

(4) Coating of Sugar Layer

In some Examples and Comparative Examples, an additional sugar layer coating was formed on the three-layer products as prepared in the above Step (3). More specifically, the coated particles (137.8 g) were fed by spray solution composed of sucrose (170.5 g) and D-mannitol (55.0 g) dissolved in water (138.0 g) to the CF-Granulator to form the sugar layer for adjustment of taste. The conditions used were same as those at protect coating except slit air temperature, 50° C. Aspartame (11.5 g) was added to provide the sweet taste for fine particles. Xanthan gum (0.4 g) which is a polysaccharide generated from natural source is useful for good mouth feeling. During spraying titanium dioxide (7.7 g) and flavor(0.4 g) were supplied in a powder state. After drying in FBD (outlet air : 67° C.) and sieving (<500 mm), the sugar layer coated product was obtained. The amount of each ingredient used are as indicated in Table 1(a).

Examples 2 to 5 and Comparative Example

The oral dosage forms were prepared in the same manner as indicated in Example 1 except that the amount of each ingredient was changed as shown in Tables 1(a) to 1(c).

TABLE 1(a)

|  | Example 1 | | | Example 2 | | |
| --- | --- | --- | --- | --- | --- | --- |
|  | Amount of Ingredient (mg/g) | % of Core Ingredient | Product % of Coated | Amount of Ingredient (mg/g) | % of Core Ingredient | % of Coated Product |
| Core Material | | | | | | |
| Sildenafil | 70.22 | 30.99 | 19.531 | 70.220 | 33.403 | 28.575 |
| talc | — | — | — | 5.500 | 2.616 | 2.238 |
| L-HPC | 32.40 | 14.30 | 9.012 | 6.500 | 3.092 | 2.645 |
| MCC | 100.00 | 44.13 | 27.813 | 88.000 | 41.861 | 35.811 |
| HPMC | 2.40 | 1.06 | 0.668 | — | — | — |
| Ca gluconate | 21.60 | 9.53 | 6.008 | 40.000 | 19.028 | 16.277 |
| Total | 226.62 | 100.00 | 63.032 | 210.220 | 100.000 | 85.546 |
| Inner Layer | | | | | | |
| HPMC | 19.00 |  | 5.284 | 3.770 |  | 1.534 |
| NE-30D | 3.80 |  | 1.057 | 7.819 |  | 3.182 |
| Mg-St | — |  | — | — |  | — |
| Talc | 3.80 |  | 1.057 | — |  | — |
| Total | 26.60 |  | 7.398 | 11.589 |  | 4.716 |
| Out Layer | | | | | | |
| E100 | 88.62 |  | 24.648 | 22.730 |  | 9.25 |
| TC-5E | — |  | — | — |  | — |
| Talc | 17.70 |  | 4.923 | — |  | — |
| Mg-St | — |  | — | 1.200 |  | 0.488 |
| Total | 106.32 |  | 29.571 | 23.930 |  | 9.738 |
| Sub-total | 359.54 |  | 100.00 | 245.739 |  | 100.000 |
| Sugar Layer | | | | | | |
| Sucrose | 444.96 |  | 123.758 | — |  | — |
| D-mannitol | 143.50 |  | 39.912 | 27.000 |  | 10.987 |
| Primojel |  |  | 3.800 |  |  | 1.546 |
| Xantan gum | 1.00 |  | 0.278 | 0.040 |  | 0.016 |
| Asparteme | 30.00 |  | 8.344 | 10.700 |  | 4.355 |
| Flavor | 1.00 |  | 0.278 | — |  | — |
| TiO2 | 20.00 |  | 5.563 | — |  | — |
| Total | 640.46 |  | 178.133 | 41.540 |  | 16.904 |
| Grand Total | 1000.00 |  | 278.134 | 287.279 |  | 116.904 |

TABLE 1(b)

|  | Example 3 | | | Example 4 | | |
|---|---|---|---|---|---|---|
|  | Amount of Ingredient (mg/g) | % of Core Ingredient | % of Coated Product | Amount of Ingredient (mg/g) | % of Core Ingredient | % of Coated Product |
| Core Material | | | | 4 | | |
| Sildenafil | 70.22 | 32.356 | 25.548 | 71.84 | 30.531 | 18.857 |
| talc | 4.40 | 2.028 | 1.601 | — | — | — |
| L-HPC | 9.40 | 4.331 | 3.420 | 57.97 | 24.637 | 15.216 |
| MCC | 110.40 | 50.871 | 40.167 | 76.57 | 32.541 | 20.099 |
| HPMC | 1.00 | 0.461 | 0.364 | 6.82 | 2.898 | 1.790 |
| Ca gluconate | 21.60 | 9.953 | 7.859 | 22.10 | 9.393 | 5.801 |
| Total Inner Layer | 217.02 | 100.000 | 78.959 | 235.30 | 100.000 | 61.763 |
| HPMC | 18.10 | | 6.584 | 18.91 | | 4.964 |
| NE-30D | 3.62 | | 1.317 | 3.79 | | 0.995 |
| Mg-St | — | | — | 0.16 | | 0.042 |
| Talc | — | | — | 3.79 | | 0.995 |
| Total Out Layer | 21.72 | | 7.901 | 26.65 | | 6.996 |
| E100 | 35.81 | | 13.030 | 91.68 | | 24.065 |
| TC-5E | — | | — | — | | — |
| Talc | — | | — | 26.20 | | 6.877 |
| Mg-St | 0.30 | | 0.110 | 1.14 | | 0.299 |
| Total | 36.11 | | 13.140 | 119.02 | | 31.241 |
| Sub Total | 274.85 | | 100.000 | 380.97 | | 100.000 |
| Sugar Layer | | | | | | |
| Sucrose | 533.15 | | 193.979 | 427.03 | | 112.090 |
| D-mannitol | 140.00 | | 50.937 | 140.00 | | 36.748 |
| Primojel | — | | — | — | | — |
| Xantan gum | 1.00 | | 0.364 | 1.00 | | 0.263 |
| Asparteme | 30.00 | | 10.915 | 30.00 | | 7.875 |
| Flavor | 1.00 | | 0.364 | 1.00 | | 0.263 |
| TiO$_2$ | 20.00 | | 7.277 | 20.00 | | 5.250 |
| Total | 725.15 | | 263.836 | 619.03 | | 162.49 |
| Grand Total | 1000.00 | | 363.836 | 1000.00 | | 262.489 |

TABLE 1(c)

|  | Example 5 | | | Comparative Example 1 | | |
|---|---|---|---|---|---|---|
|  | Amount of Ingredient (mg/g) | % of Core Ingredient | % of Coated Product | Amount of Ingredient (mg/g) | % of Core Ingredient | % of Coated Product |
| Core Material | | | | 4 | | |
| Sildenafil | 71.84 | 30.531 | 19.589 | 70.22 | 30.801 | 15.865 |
| talc | — | — | — | — | — | — |
| L-HPC | 57.97 | 24.637 | 15.807 | 21.60 | 9.475 | 4.880 |
| MCC | 76.57 | 32.541 | 20.879 | 110.40 | 48.425 | 24.944 |
| HPMC | 6.82 | 2.898 | 1.860 | 1.30 | 0.570 | 0.294 |
| Ca gluconate | 22.10 | 9.393 | 6.025 | 21.60 | 9.475 | 4.880 |
| polysorbate 80 | — | — | — | 0.76 | 0.333 | 0.172 |
| Citric acid | — | — | — | 2.10 | 0.921 | 0.474 |
| Total Inner Layer | 235.30 | 100.000 | 64.160 | 227.98 | 100.000 | 51.509 |
| HPMC | 18.91 | | 5.156 | 18.91 | | 4.272 |
| NE-30D | 3.79 | | 1.033 | 3.79 | | 0.856 |

TABLE 1(c)-continued

|  | Example 5 | | | Comparative Example 1 | | |
|---|---|---|---|---|---|---|
|  | Amount of Ingredient (mg/g) | % of Core Ingredient | % of Coated Product | Amount of Ingredient (mg/g) | % of Core Ingredient | % of Coated Product |
| Mg-St | 0.16 |  | 0.044 | — |  | — |
| Talc | 3.79 |  | 1.033 | 1.37 |  | 0.310 |
| Total Out Layer | 26.65 |  | 7.266 | 24.07 |  | 5.438 |
| E100 | 73.35 |  | 20.001 | 189.05 |  | 42.714 |
| TC-5E | 18.34 |  | 5.001 | — |  | — |
| Talc | 13.10 |  | 3.572 | — |  | — |
| Mg-St | — |  | — | 1.50 |  | 0.339 |
| Total | 104.79 |  | 28.574 | 190.55 |  | 43.053 |
| Sub-total Sugar Layer | 366.74 |  | 100.000 | 442.60 |  | 100.000 |
| Sucrose | 441.26 |  | 120.320 | 365.40 |  | 82.558 |
| D-mannitol | 140.00 |  | 38.174 | 140.00 |  | 31.631 |
| Primojel | — |  | — | — |  | — |
| Xantan gum | 1.00 |  | 0.273 | 1.00 |  | 0.226 |
| Asparteme | 30.00 |  | 8.180 | 30.00 |  | 6.778 |
| Flavor | 1.00 |  | 0.273 | 1.00 |  | 0.226 |
| TiO2 | 20.00 |  | 5.453 | 20.00 |  | 4.519 |
| Total | 633.26 |  | 172.673 | 557.40 |  | 125.94 |
| Grand Total | 1000.00 |  | 272.673 | 1000.00 |  | 225.938 |

EXPERIMENTS (1) Bitterness Test

Five (5) panelists held 1 g of the three or four layered products prepared by the above procedures in their mouth for 1 min, and measured a time period until they felt bitterness. The average time (in seconds) was used for evaluation. The desirable masking time period is more than 50 seconds. The results are indicated in Table 2.

(2) Drug Release Test

According to the guideline published by Minister of Health and Welfare (MHW) in Japan, the dissolution test were conducted in each three media (pH 1.2, 4.0, and 6.5). Further, the dissolution tests in media of pH5.0, 5.5, 6.0 were also investigated to predict the in vivo dissolution of lower- and non-gastric acidity humans. The release experiments from the particles were performed by the Japanese Pharmacopeia (JP) paddle method in 900 ml of media at 37° C. The three or four layered products prepared in the above procedures were spread over the media with constant stirring at 100 rpm. The media used in this study were the 1st fluid (disintegration test fluid, Japanese Pharmacopoeia 13, pH1.2), 0.1M acetate buffer (pH4.0), and 0.05M phosphate buffers (pH5.5, 6.0, 6.5). The drug release properties were evaluated as the amount of the drug released after 5, 10 and 15 minutes from the introduction of the drugs into each media. The results are indicated in Table 2.

TABLE 2

|  | Examples | | | | | Comp. Example | Desirable Value |
|---|---|---|---|---|---|---|---|
|  | 1 | 2 | 3 | 4 | 5 | | |
| Bitterness Test (sec.) | >120 | >55 | >75 | >120 | >53 | >120 | >50 sec. |
| (Drug Release Test) | | | | | | | |
| RA (%, pH 1.2 after 5 min.) | 103.1 | | | | | | |
| RA (%, pH 1.2 after 10 min.) | 101.6 | | | | | | |
| RA (%, pH 1.2 after 20 min.) | 102.2 | | | | | | >75% |
| RA (%, pH 4.0 after 5 min.) | 87.7 | 71.3 | | 90.4 | | | |
| RA (%, pH 4.0 after 10 min.) | 98.8 | 86.7 | 83.5 | 98.7 | | 90.4 | |
| RA (%, pH 4.0 after 20 min.) | 100.0 | 95.7 | 95.5 | 99.3 | | 99.7 | >75% |
| RA (%, pH 5.5 after 5 min.) | | | | | | | |
| RA (%, pH 5.5 after 10 min.) | 95.8 | | | | | | |
| RA (%, pH 5.5 after 20 min.) | 95.6 | 90.5 | 86.6 | 90.5 | 93.9 | 74.3 | >75% |
| RA (%, pH 6.0 after 5 min.) | | | | | | | |
| RA (%, pH 6.0 after 10 min.) | 87.0 | | | | | | |
| RA (%, pH 6.0 after 20 min.) | 87.7 | | | | | | >75% |
| RA (%, pH 6.5 after 2.5 min.) | 2.0 | | | 2.1 | 18.2 | | |
| RA (%, pH 6.5 after 5 min.) | 20.3 | 31.1 | 43.5 | 8.9 | 49.0 | | |
| RA (%, pH 6.5 after 20 min.) | 44.9 | 33.1 | 45.6 | 37.5 | 60.3 | 5.4 | >30% |

As shown in Table 2, it was confirmed that the oral dosage forms of this invention (Examples 1 to 5) have good taste masking properties and good drug release profiles.

More specifically, the time period until panelists felt bitterness showed more than 50 sec. in all examples. Further, it was found that the oral dosage forms of this invention have fast onset release profiles in media within a range of pH1.2 to pH5.5 (gastric juice). It was reported that pH values of the empty stomach in thirty subjects varied from less than 2 to 5.5. It was also confirmed that the release profiles, of the products of this invention, in media of pH value ranging 1.2 to 5.5 were satisfactory even in the case of lower- and non-acidity humans.

Further, normal humans have a saliva with a pH value of about 6.5, and thus small drug release amount after 2.5 minutes stirring from administration in the media with pH 6.5 is preferable. The release profiles, at pH6.5, of the products of this invention showed the sigmoidal release pattern, that is, the rapid release profile after the time lag for a few minutes. This is a good drug release profile since some aged patients have a gastric juice with a pH value of about 6.5. In this case, preferably the drug should be released in an amount of more than 30% after 20 minutes stirring. The desirable dissolution value at 20 min, was 30% (pH6.5) rather than 75% (pH 1.2, 4.0, 5.5, 6.0), since the solubility of sildenafil at pH6.5 is low. All the products of this invention showed a drug release percentage, at pH 6.5 after 20 minutes stirring, of more than 30% although the product prepared in the Comparative Example showed a drug release percentage of only 5.4.

In summary, it was substantiated that the oral dosage forms of this invention have good drug release properties and good taste-masking properties.

What is claimed is:

1. A rapidly releasing and taste-masking pharmaceutical dosage form comprising a core containing a pharmaceutically active ingredient, low-substituted hydroxypropyl cellulose containing not less than 5.0% and not more than 16.0% hydroxypropoxy groups on a dried basis, and microcrystalline cellulose, the amount of the microcrystalline cellulose being at least 26.0 weight percent based on the total weight of the core; an inner coating layer formed on the core and containing a water-soluble polymer; and an outer coating layer formed on the inner coating layer and containing a saliva-insoluble polymer, wherein the core, the inner coating layer and the outer coating layer are contained in an amount of from 60.0 to 87.0, from 4.0 to 31.0 and from 9.0 to 36.0 weight percent, respectively, based on the total weight of the dosage form.

2. A dosage form according to claim 1, which is further coated by a sugar coating layer formed on the outer coating layer in an amount of 15.0 to 270.0 weight percent based on the total weight of a coated particle composed of the core, the inner and outer coating layers.

3. A dosage form according to claim 1, wherein the core is in a spherical form and has an average particle diameter of 80 to 400 micrometers.

4. A dosage form according to claim 1, wherein the core comprises 0.1 to 73.5 weight percent of the active ingredient, 26.0 to 99.4 weight percent of the microcrystalline cellulose and 0.5 to 34.0 weight percent of the low-substituted hydroxypropyl cellulose, the weight percent being based on the total weight of the core material.

5. A dosage form according to claim 1, wherein the core comprises 20.0 to 40.0 weight percent of the active ingredient, 30.0 to 60.0 weight percent of the microcrystalline cellulose and 3.0 to 30.0 weight percent of the low-substituted hydroxypropyl cellulose, the weight percent being based on the total weight of the core material.

6. A dosage form according to claim 1, wherein the inner coating layer comprises 70.0 to 100 weight percent of a water-soluble polymer selected from hydroxypropylmethyl cellulose and hydroxypropyl cellulose; and up to 30.0 weight percent of a water-insoluble polymer selected from an ethylcellulose, a methacrylate copolymer and an aminoalkyl methacrylate copolymer, the weight percent being based on the total weight of the inner coating layer.

7. A dosage form according to claim 1, wherein the outer coating layer comprises 70.0 to 100 weight percent of a saliva-insoluble polymer selected form polyvinylacetal diethylaminoacetate and butyl methacrylate/(2-dimethylaminoethyl)methacrylate/methyl methacrylate copolymer; and up to 30 weight percent of a water soluble or water-insoluble polymer selected from hydroxypropylmethyl cellulose, hydroxypropyl cellulose, ethylcellulose, an ethyl acrylate/methyl methacrylate/trimethylammonioethyl methacrylate copolymer, the weight percent being based on the total weight of the outer coating layer.

8. A process for preparing a dosage form of claim 1, which comprises mixing core materials containing a pharmaceutically active ingredient, low-substituted hydroxypropyl cellulose and microcrystalline cellulose, and subjecting the mixed core materials to wet agitation granulation, dry treatment and sieving treatment in this order to obtain core particles; forming an inner coating layer on the core particles by spraying with an aqueous solution containing a water-soluble polymer; and then forming an outer coating layer on the inner coating layer by spraying with an aqueous solution containing a saliva-insoluble polymer.

9. A process according to claim 8, which is carried out in the absence of a solvent harmful to a human body.

* * * * *